March 21, 1950 E. S. BOERNER Plant Pat. 926
ROSE PLANT
Filed March 8, 1949
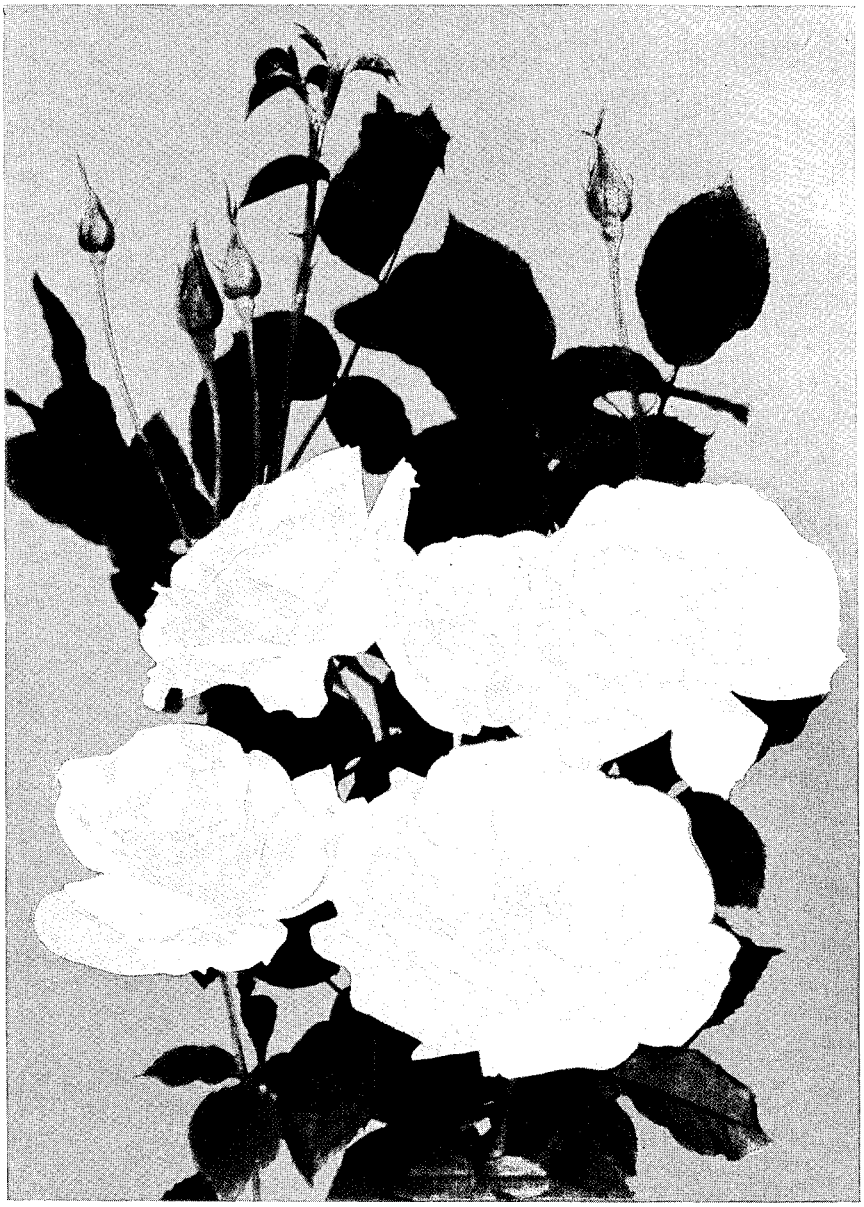
Inventor
E. S. Boerner
By Robb & Robb
Attorneys Patented Mar. 21, 1950

UNITED STATES PATENT OFFICE

926

ROSE PLANT

Eugene S. Boerner, Newark, N. Y., assignor to Jackson & Perkins Company, Newark, N. Y., a corporation of New York Application March 8, 1949, Serial No. 80,293

1 Claim. (Cl. 47—61)

The present invention relates to a new and distinct variety of rose plant, originated by crossing a floribunda rose "Pinocchio" with a hybrid tea, "Crimson Glory."

This new variety resulting from said cross is characterized as to novelty by a new color of bloom in the class of floribundas, a color which lies between Rose Red and Tyrian Rose, as hereinafter more specifically referred to by the mass of blooms produced; by its intermittent habit of blooming; and the perfection of shape of the flower which holds its form to the end. More specifically speaking, it has retained many of the plant habits of "Pinocchio"; the bud form has retained the characteristics of "Pinocchio," but the open flower is more single and has definitely different characteristics than either of its parents.

Asexual reproduction of this new variety shows the foregoing characteristics come true to form and are established.

The accompanying drawing discloses specimens of this new variety showing clearly the development of the flower from bud to full blown stages of development.

The following is a detailed description of the new variety, color terminology being in accordance with Ridgway's Color Standards and Nomenclature:

Parentage: Seedlings.
- *Seed parent.*—"Pinocchio" (Pl. Pat. No. 484).
- *Pollen parent.*—"Crimson Glory" (Pl. Pat. No. 105).

Classification:
- *Botanic.*—Large flowered polyantha.
- *Commercial.*—Floribunda.

*Flower*

Blooming habit (this plant was asexually reproduced by budding at Newark, New York, and at Pleasanton, California, but the observations hereinafter were made in fields at Newark, New York, in the month of October, in the morning): Recurrent—intermittent.

Bud:
- *Size.*—Large.
- *Form.*—Ovoid. Is not affected by wet or hot weather.
- *Color.*—When sepals first divide—Oxblood Red, Plate 1. When petals begin to unfurl—Spinel Red, Plate 26. When half blown—inside of petals—Rose Red, Plate 12; reverse of petals—Tyrian Rose, Plate 12.

- *Sepals.*—Serrated; branched. Curl back when petals begin to unfurl. Color—inside—Light Turtle Green, Plate 32; outside—Light Hellebore Green, Plate 17.
- *Calyx.*—Shape—funnel. Size—small. Aspect—smooth. Odor when rubbed—none. Color—Yellowish Oil Green, Plate 5.
- *Peduncle.*—Length—short. Aspect—smooth. Color—Light Elm Green, Plate 17. Strength—erect; slender.
- *Opening*—Bud opens up well. Is not affected by adverse weather conditions.

Bloom:
- *Size.*—Large. Average size when fully expanded, 3½"-4½".
- *Borne.*—In irregular clusters.
- *Stems.*—Medium length; strong.
- *Form.*—When first open—high center. Permanence—retains its form to the end.
- *Petalage.*—Double (full but open center). Number of petals under normal conditions, 25.
- *Color.*—Center of flower—Begonia Rose, Plate 1. Outer petals—Begonia Rose, Plate 1, overcast with Deep Rose Pink, Plate 12. Base of petals (aiglet)—Citron Yellow, Plate 16. Inside of petals—between Rose Red, Plate 12, and Tyrian Rose, Plate 12. Reverse of petals—between Tyrian Rose, Plate 12, and Rose Color, Plate 12. General tonality from a distance—between Rose Red, Plate 12, and Tyrian Rose, Plate 12.
- *Discoloration.*—General tonality at end of first day—Begonia Rose, Plate 1. Second day—between Rose Red, Plate 12, and Tyrian Rose, Plate 12. Third day—Tyrian Rose, Plate 12.

Petals:
- *Texture.*—Leathery. Is not affected by wet or hot weather.
- *Appearance.*—Inside—satiny; outside—shiny.
- *Form.*—Oval.
- *Arrangement.*—Imbricated (regularly arranged shinglelike). Petaloids in center—few; small.
- *Persistence.*—Drop off cleanly.
- *Fragrance.*—Moderate. Nature—tea (average hybrid tea scent).
- *Lasting quality.*—On the plant and as cut flower—long.

Genital organs:
- *Stamens, anthers.*—Medium size; many.

Color—Apricot Yellow, Plate 4. Arrangement—regular around styles.

*Stamens, filaments (threads).*—Medium length. Color—Buff Yellow, Plate 4.

*Pollen.*—Maize Yellow, Plate 4.

*Styles.*—Bunched, uneven length; medium length; thin.

*Stigmas.*—Light Buff, Plate 15.

*Ovaries.*—All enclosed in calyx.

*Plant*

Form: Bush.

Growth: Vigorous; compact.

Foliage: 5–7 leaflets.

*Size.*—Medium.

*Quantity.*—Normal.

*Color.*—New foliage: upper side—Oil Green, Plate 5; serrations and mid-rib Oxblood Red, Plate 1; under side—Yellowish Oil Green, Plate 5, overcast with Oxblood Red, Plate 1. Old foliage: upper side—Dark Cress Green, Plate 31; under side—Light Elm Green, Plate 17.

*Shape.*—Oval pointed.

*Texture.*—Upper side—glossy. Under side—smooth. Ribs and veins—ordinary.

*Edge.*—Serrated (saw toothed).

*Serration.*—Single; small.

*Leaf stem.*—Light Cress Green, Plate 31. Under side—prickles.

*Stipules.*—Medium length; smooth.

*Disease resistance.*—Resistant.

Wood:

*New wood.*—Color—Garnet Brown, Plate 1. Bark—smooth.

*Old wood.*—Color—Jade Green, Plate 31. Bark—smooth.

Thorns:

*Thorns.*—Quantity—on main stalks from base—many; on laterals from stalk—ordinary. Form—narrow base; medium length; straight. Color when young—Oxblood Red, Plate 1. Position—irregular.

*Prickles and hairs.*—none.

I claim:

A new and distinct variety of floribunda rose plant characterized as to novelty by the color of its bloom; the mass production of blooms; intermittent habit of blooming and its perfectly shaped flower which holds its form to the end, substantially as shown and described.

EUGENE S. BOERNER.

No references cited.